United States Patent [19]
Merjanian

[11] Patent Number: 6,041,134
[45] Date of Patent: *Mar. 21, 2000

[54] ERGONOMIC FINGERPRINT READER HOUSING

[75] Inventor: John Michael Merjanian, Burlington, Mass.

[73] Assignee: The National Registry, Inc., St. Petersburg, Fla.

[*] Notice: This patent is subject to a terminal disclaimer.

[21] Appl. No.: 09/248,063

[22] Filed: Feb. 10, 1999

Related U.S. Application Data

[63] Continuation of application No. 08/836,242, filed as application No. PCT/US95/14374, Oct. 28, 1995, Pat. No. 5,920,642.

[51] Int. Cl.⁷ ...................................................... G06K 9/00
[52] U.S. Cl. .......................... 382/126; 382/124; 382/115
[58] Field of Search .................................... 382/124, 126, 382/127, 115

[56] References Cited

U.S. PATENT DOCUMENTS

| | | | |
|---|---|---|---|
| 3,668,633 | 6/1972 | Sadowsky | 382/126 |
| 3,804,524 | 4/1974 | Jocoy et al. | 356/138 |
| 3,865,488 | 2/1975 | Del Rio | 356/71 |
| 3,975,711 | 8/1976 | McMahon | 382/126 |
| 4,053,228 | 10/1977 | Schiller | 356/71 |
| 4,153,970 | 5/1979 | Perkinson | 16/111 R |
| 4,202,120 | 5/1980 | Engel | 283/99 |
| 4,385,831 | 5/1983 | Ruell | 356/71 |
| 4,455,083 | 6/1984 | Elmes | 356/71 |
| 4,684,802 | 8/1987 | Hakenewerth et al. | 250/235 |
| 4,728,186 | 3/1988 | Eguchi et al. | 356/71 |
| 4,783,167 | 11/1988 | Schiller et al. | 356/71 |
| 4,857,916 | 8/1989 | Bellin | 382/4 |
| 4,905,293 | 2/1990 | Asai et al. | 382/126 |
| 4,924,085 | 5/1990 | Kato et al. | 250/227.28 |
| 4,993,068 | 2/1991 | Piosenka et al. | 380/23 |
| 5,067,162 | 11/1991 | Driscoll, Jr. et al. | 382/126 |
| 5,103,486 | 4/1992 | Grippi | 382/4 |
| 5,144,680 | 9/1992 | Kobayashi et al. | 382/124 |
| 5,546,471 | 8/1996 | Merjanian | 382/124 |
| 5,565,857 | 10/1996 | Lee | 340/825.34 |
| 5,748,765 | 5/1998 | Takhar | 382/124 |

Primary Examiner—Jose L. Couso
Assistant Examiner—Anh Hong Do
Attorney, Agent, or Firm—Darby & Darby

[57] ABSTRACT

A housing in accordance with the invention includes a platen therein having a platen surface adapted to be contacted by a digit of a person's hand and first and second exterior surfaces. The first surface has an aperture, and the platen surface is in register with the aperture for contact by a digit. The second surface is displaced from the first to provide a grasping surface. The housing is shaped to orient the digit relative to the platen to ensure a firm grip of the housing and is also shaped such that the second surface contacts four digits of the user's hand while a chosen, fifth digit is positioned on the platen. A further, optional feature is base which is shaped to support the housing so that the housing is universally positionable in the base to a preselected position for grasping the first and second surfaces and acquiring the print. A fingerprint acquisition device including the foregoing housing construction further houses a light source for irradiating the platen surface and any digit thereon with light, a light conductor for conveying light from the irradiated platen surface, and an image sensor for sensing the conducted light.

20 Claims, 6 Drawing Sheets

ERGONOMIC FINGERPRINT READER HOUSING

This is a continuation of the U.S. patent application No. 08/836,242, field on Apr. 28, 1997, now U.S. Pat. No. 5,920,642, which is a 371 of PCT/U.S. 95/14374, filed on Oct. 28, 1995.

FIELD OF THE INVENTION

The present invention relates to fingerprint acquisition systems, and more particularly to an ergonomic apparatus for acquiring fingerprint data from a person's digit.

BACKGROUND OF THE INVENTION

One known method for verifying or authenticating that a particular person is the same person who had previously been identified is to compare that person's fingerprint to a previously obtained fingerprint. According to one conventional method of acquiring fingerprint data, an ink impression of a fingerprint is printed on paper for subsequent scanning into a digital computer. According to this method, the finger is stained with ink each time the fingerprint data is entered. Any uneven coating or blurring of the ink hinders the input operation, as does any lateral motion or shear of the inked finger when applied to the paper. To ensure that enough information is obtained during data input or enrollment, the finger is typically "rolled" across the paper to transfer a greater portion of the surface of the person's finger thereto. While the rolling step increases the overall amount of data acquired, the increased risk of finger shear undermines the integrity of the acquired data. Further, geometric or electronic distortions may be introduced during the process of scanning the data into the digital computer.

According to more modern methods, fingerprints are obtained by reflecting or scattering an image of the finger surface onto an image sensor, such as a charge coupled device. Devices that perform this function are described in, for example, U.S. Pat. Nos. 4,924,085 to Kato et al., 5,088,817 to Igaki et al., and 5,067,162 to Driscoll, Jr., et al., the disclosures of which are hereby incorporated by reference as though set forth in their entirety herein. In each of these systems, a light source is irradiated at a reflected angle onto the ridge and groove portions of a fingerprint which has been pressed against a light conducting plate. Depending upon the particular orientation of the light source with respect to the light conducting plate, and the location of the image sensing device, either the reflected or the scattered light from the fingerprint is measured. The image sensor captures the measured light so that the captured fingerprint data can be stored. While these modern methods have simplified the fingerprint data acquisition process, they have not provided a system which ensures that the finger apply even pressure to the platen to obtain a broad print.

One graspable system for identifying an individual is taught in U.S. Pat. No. 4,857,916. This system identifies an individual using a plurality of pressure sensors located across a graspable member for developing a uniquely identifying signal indicative of the pressures exerted by an individual's hand in grasping the graspable member. This system does not acquire the person's fingerprint data, but rather utilizes the pressure points to construct identifying data.

While there has been recognition in the art of the need to position a finger with respect to the finger platen, see for example Kato et al., what has been needed and has heretofore not been fulfilled in the art, is a fingerprint reader apparatus which provides a prehensile shape to permit grasping the fingerprint reader device in a manner so that the person's digit applies even pressure to the platen and thereby allows a broad, even print of the digit to be acquired. Also needed is a fingerprint reader apparatus that provides a prehensile shape with the aforementioned advantages, packaged in a wireless housing for communication with a remote receiving device. Of further benefit to the art, would be such a system that further allows notarization of transactions to authenticate that a transaction to be charged against an account has been authorized by an account holder. The present invention satisfies these and other needs in an ergonomic fingerprint reader apparatus.

SUMMARY OF THE INVENTION

In accordance with one aspect of the invention, there is provided an ergonomic housing for acquiring a broad, even print of a fingerprint from a person's digit. The housing has at least first and second surfaces, the first surface having an aperture so that a person can place his or her digit on an image transfer platen disposed in register with the aperture. The second surface is displaced from the first surface to provide a grasping surface, and may be substantially opposite the first surface except when the second surface is spherical, as in one embodiment. The housing is provided with a prehensile shape to permit grasping the first and second surfaces within a hand of the person while the person's digit is or presses on the platen so that the digit applies even pressure to the platen and a broad print of the digit is acquired.

In accordance with another aspect of the invention, the housing includes a contoured surface adjacent the aperture. The contoured surface may have a digit guide for guiding the person's digit onto the platen. Also, the contoured surface may have a ramp for ramping the person's digit onto the platen at an angle such that the digit contacts or presses the platen at an increased number of locations. As a further feature, the housing may have a tactile feedback indicator for providing tactile feedback to the person whose print is being acquired of the location of the digit on the platen.

In another embodiment of the invention, the first and second surfaces are joined at one margin so that the ergonomic housing can flex when the first and second surfaces are grasped and perhaps squeezed within the hand of the person while the person's digit is or presses on the platen. In this manner, the ergonomic housing generally distributes pressure from the person's hand across the housing and the platen.

In accordance with still another aspect of the invention, an ergonomic fingerprint acquisition device is provided. The acquisition device comprises a housing having first and second exterior surfaces, the housing enclosing: a platen; a light source for irradiating the platen and any digit thereon with light; means for conducting light from the irradiated platen; and image sensing means for sensing the conducted light. The first exterior surface of the housing has an aperture therethrough, and the platen is disposed in register with the aperture so that a person can place his or her digit on the platen. The second exterior surface is displaced from the first exterior surface to provide a grasping surface. The housing is provided with a prehensile shape to permit grasping the first and second exterior surfaces within a hand of the person while the person's digit is or presses on the platen so that the digit applies even pressure to the platen and a broad print of the digit is acquired at the image sensing means. Any print acquired at the image sensing means may be conveyed to a remote location by a conductive wire, optical cable, infrared, inductive pickup, or radio frequency. In addition, the ergonomic fingerprint acquisition device may have data extracting means for extracting data from a credit card or food stamp and perhaps matching means for matching any acquire into the extracted data, and even perhaps verification means for indicating that the acquired print and the extracted data match.

According to yet still another aspect of the invention, there is provided a notarizing system for authenticating that a transaction to be charged against an account has been authorized by an account holder. The notarization system includes fingerprint acquisition means for acquiring a print from an operator's digit, at least part of the acquired print forming a first signal component; account identifying means for identifying the account against which the transaction is to be charged, the identified account forming a second signal component; means for conveying the first and second signal components to a remote location; comparison means at the remote location for comparing the first signal component to stored fingerprint data for the operator and for comparing the second signal component to stored account for the identified account; and authenticating means for confirming that the operator is authorized to charge the transaction against the identified account.

According to a further aspect of the invention, there is provided a remote control in combination with a set-top box for use with a television set of the type that provides one or more operators with adjustable features including an adjustable service level and preference setting. The combination comprises a fingerprint reader, the fingerprint reader including fingerprint acquisition means for acquiring a print from an operator's digit as a fingerprint signal; conveying means for conveying the fingerprint signal to the set-top box; comparison means at the set-top box for comparing the fingerprint signal to stored fingerprint data for a match; and means responsive to any match for adjusting one of the service level and the preference setting. The combination allows the service level to be adjusted in response to a fingerprint match to provide access to channels for which access is normally restricted, for example, so that children or house guests—whose fingerprint data are unknown to the system—can not order pay-per-view events or other services without the assistance of an authorized person—whose fingerprint data are known and configured to authorize such access. The combination may further have storage means within the set-top box for storing the preference setting for several operators to allow the preference setting to be adjusted to each operator in response to a fingerprint match by restoring the stored preference setting for that operator. The remote control of the combination is preferably contained within a prehensile housing, as described above.

DETAILED DESCRIPTION OF THE INVENTION

Figure 1:
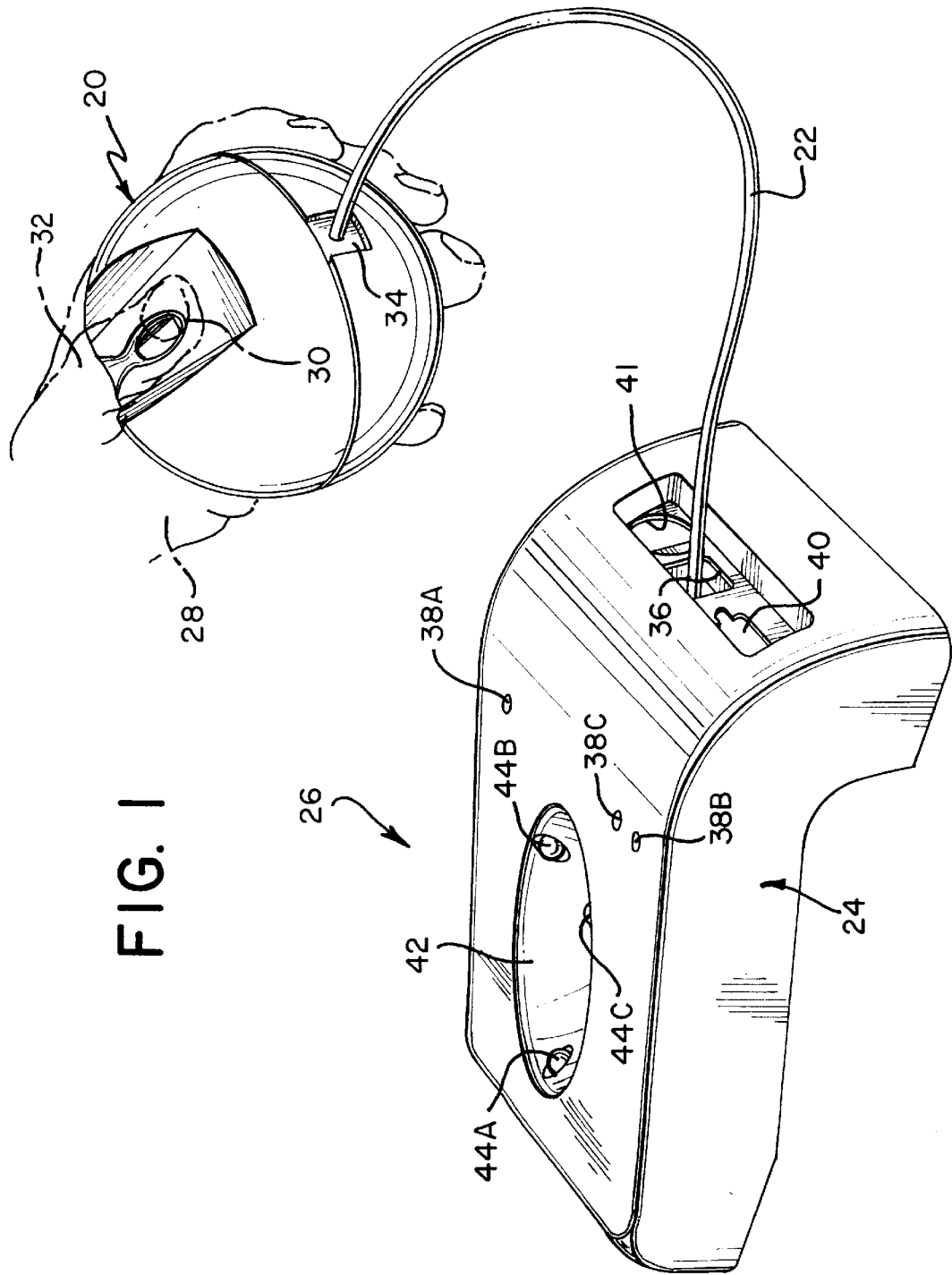
FIG. 1 shows a perspective view of the first embodiment of the ergonomic fingerprint reader apparatus of the present invention attached to a base by a tether cord.

Referring now to FIG. 1, there seen an ergonomic fingerprint reader apparatus 20 according to one embodiment of the present invention. The ergonomic apparatus 20 is connected by a tether 22 to a base unit 24 to comprise a fingerprint reading system 26. In FIG. 1, a hand 28 has grasped the ergonomic reader 20 and has placed a digit 32 on a platen 30. The platen 30 serves as an image transfer surface upon which the image from the digit 32 is conveyed to an image sensing device. The image sensing device converts the optical image from a top surface of the platen 30 to an electronic signal for transmission through wires or optical cables (not shown) within the tether 22 into the base 24. The tether 22 is connected to the ergonomic reader 20 at a port 34 and to the base 24 at a port 36.

It has been observed that the physical form of the ergonomic reader is less intimidating than prior art designs, thereby placing the operator somewhat at ease at the prospect of providing his or her fingerprint for authentication or verification. Also, because the operator need not place his or her digit 32 inside any of the foregoing ergonomic devices, any existing intimidation factor of using the ergonomic fingerprint reader is again reduced. When used with an LED that emits light that is approximately 530 nanometers in wavelength which appears green to the eye, the irradiated platen provides a soothing appearance to further reduce any intimidation.

In the simplified diagram of FIG. 1, the base 24 is illustrated as having a plurality of lights 38A,B,C which indicate the status of the system 26, or perhaps other information. For example, the light 38A may indicate that the system 26 is on, while lights 38B,C may be utilized to indicate whether information is being transferred between the ergonomic reader 20 and the base 24 through the tether 22, or from the base 24 to an external device through a serial interface 40. The serial interface 40 is used to connect the system 26 to an external device, for example, a computer or modem, and a power port 41 connects the system to a source of power. Of course, additional lights 38 or more sophisticated displays (for example, seven-segment LEDs, LCD screens, color monitor, etc.) can be provided.

Figure 1A:
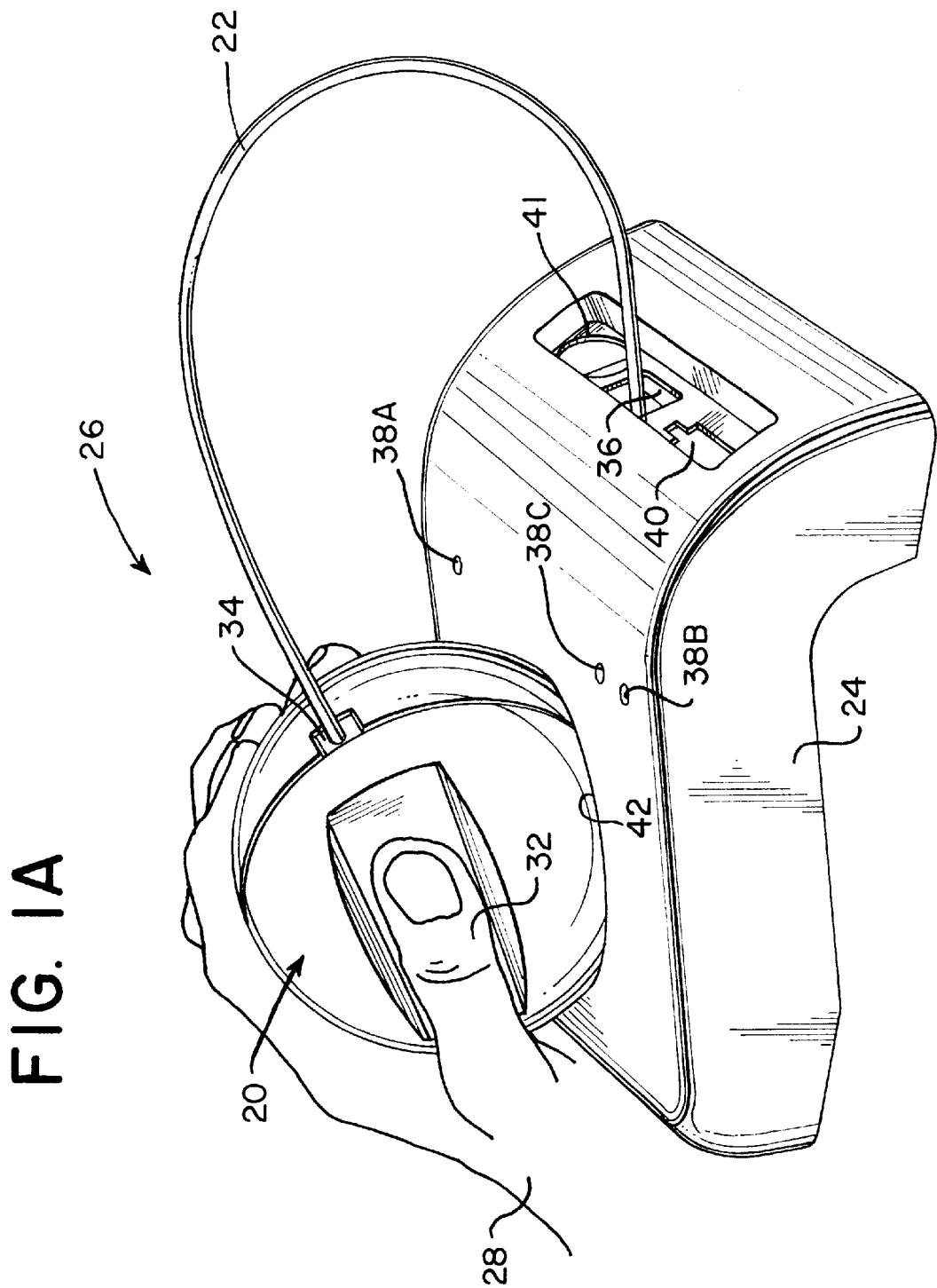
FIG. 1A shows a perspective view of the ergonomic fingerprint reader apparatus of FIG. 1 being operated within the base.

Once the operator has input fingerprint data using the ergonomic reader 20, the reader 20 may be returned to the base for storage, for example, in the recess 42. The recess 42 may be provided with a plurality of protuberances 44A,B,C which preferably form a friction coupling between the ergonomic reader 20 and the base 24 sufficient to maintain the position of the ergonomic reader within the base until repositioned by the hand 28. In this regard, the base 24 provides a presentation structure for the ball-like ergonomic reader 20. Rather than grasping the ergonomic reader 20 in the hand 28, the user may adjust the ergonomic reader 20 within the recess 42 to a preferred position and operate it with equal facility within the base 24 by cradling the ergonomic reader 20 within the base 24, as shown in FIG. 1A.

Figure 2:
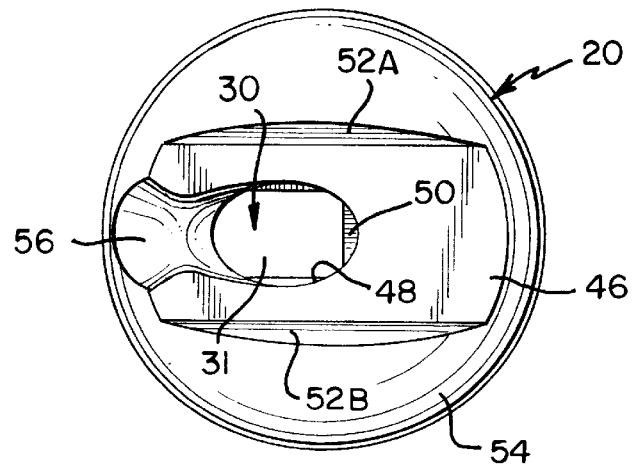
FIG. 2 is a top view of the ergonomic apparatus of FIG. 1.

With reference now to FIG. 2, there is seen a top view of the ergonomic reader 20 of FIG. 1. As seen in FIG. 2, the platen 30 sits in a generally planar surface 46, although the invention is not so limited. The planar or first exterior surface 46 has an aperture 48 through which a top surface 31 of the platen 30 is exposed. The aperture 48 preferably is formed as an ellipse with a major and minor axis. In this embodiment, the ellipse has a major axis that is 28 mm long and a minor axis that is 22 mm long. Between the platen top surface 31 and the planar surface 46 is an edge 50 that provides tactile feedback to the operator as to the location of the digit 32 on the platen 30. The edge 50 extends approximately 3 mm normal to the top surface 31 in a preferred embodiment. Walls 52A,B flank either side of the planar surface 46 and extend therefrom to an outside or second exterior surface 54. The walls 52 are depicted as inclined to facilitate access to the planar surface 46. According to one aspect of the invention, a contoured surface 56 is provided adjacent the planar surface 46 in abutting relationship to the platen 30. The contoured surface 56 is described in detail below in connection with FIGS. 4 and 4A.

In the embodiment of FIGS. 1–4A, the ergonomic reader 20 has a spherical shape, and the form factor of a softball, that is, the ergonomic reader 20 is approximately 95 mm in diameter. In accordance with one aspect of the invention, this permits the ergonomic reader 20 to be readily grasped in the hand 28 of an operator while one digit 32 rests or presses on the platen 30. As a result of this configuration and form factor, the operator applies even pressure to the platen 30 from the natural grasping of the ergonomic reader 20. The prehensile shape of the ergonomic reader 20 allows the hand 28 to wrap around the fingerprint apparatus in a manner that permits uniform pressure to be applied to platen 30. Further, the natural grasp of the hand 28 around the ergonomic reader 20 ensures a firm grip of the fingerprint reader and reduces the likelihood of lateral movement or shear of the digit 32 on the platen 30 as data is being acquired. This further facilitates the acquisition of a broad, clear print.

Applicant has determined that a prehensile shape greatly improves the ability to acquire uniform fingerprint data for comparison to previously stored data. The stored data may be on a credit card, a smart card (that is, a pocket sized card containing a processor and memory), a local storage device, or even a central storage device at a remote location. The specific shape chosen for a particular application being a matter of design choice, all that is important to the invention is that the housing be provided with a prehensile shape. With regard to the spherical shape of the ergonomic reader 20, the reader provides a space efficient package to minimize the amount of workspace that it occupies.

The prehensile shape allows the platen to be presented to the user statically in the base 24 or dynamically in the user's hand 28. The shape readily presents the platen to a left or right hand preference individual, whether the individual is standing or seated. As such, the prehensile shape has utility to all persons, including those with limited motion ability who may need the assistance of another in presenting their digit 32 to the platen 30.

Figure 3:
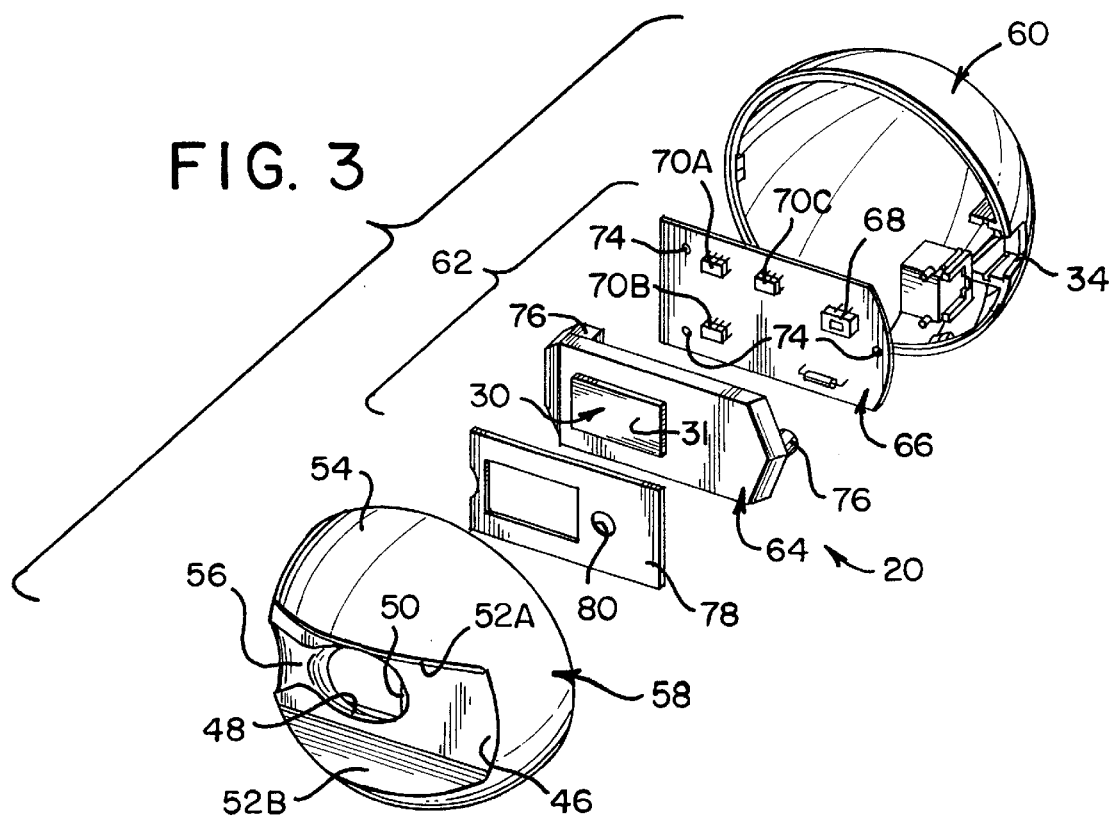
FIG. 3 is an exploded view of the ergonomic apparatus of FIG. 1.

FIG. 3 shows an exploded view of the ergonomic reader 20. The ergonomic reader 20 has first and second hemispherical portions 58,60 that house an uneven surface detection system 62, as described in co-pending application Ser. No. Unassigned to Hebert et al., for UNEVEN SURFACE IMAGE TRANSFER APPARATUS, filed on even date with this application, the disclosure of which is hereby incorporated by reference as if set forth in their entirety herein. More particularly, the uneven surface detection system 62 comprises an optical plate 64 having the platen 30 on one side thereof and a printed circuit board (PCB) 66 on the other side thereof. The PCB 66 includes an image sensing device 68 upon which images from the platen 30 are conveyed, and a complement of other electronic components 70A,B, . . . N. While the optical plate 64 may be of conventional design, it is preferred that it be of the type described in detail in the aforementioned co-pending application.

The first hemispherical portion 58 has the planar surface 46 and the aperture 48. The aperture 48 is aligned with the platen 30 of the uneven surface detection system 62 prior to assembling the first and second hemispherical portions 58, 60. The uneven surface detection system 62, which generally comprises the PCB 66 and the optical plate 64, is assembled as a unit by means of through-holes 74 which align with posts 76 extending from one side of the optical plate 64. Preferably, the posts 76 are threaded to receive screws (not shown). A piece of structural foam adhesive tape 78 is interposed between the assembly of the uneven surface detection system 62 and the first hemispherical portion 58 to seal the optical plate 64 portion of the system 62 into contact with the first hemispherical portion. The tape 78 also serves as a gasket to block light and otherwise insulate the optical plate 64 from contact with the first hemispherical portion. This precludes contact with the optical plate 64 which could otherwise interfere with the conveyance of information from the platen 30 to the image sensing device 68. An aperture 80 is provided in the tape 78 so that necessary reflections internal to the optical plate will not be interfered with at the interface of the optical plate and the tape 78, as best appreciated with reference to the aforementioned co-pending application. The particular details of the optical plate 64 are not critical to the present invention, and no further discussion thereof is provided herein.

The second hemispherical portion 60 is snap-fit into contact with the first hemispherical portion 58 to complete the assembly. The port 34 may be contained within this second hemispherical portion, along with other electronics, for example, circuitry related to fingerprint data compression, analysis, or both, or related to other electronic functions such as wireless communication, etc.

Figure 4:
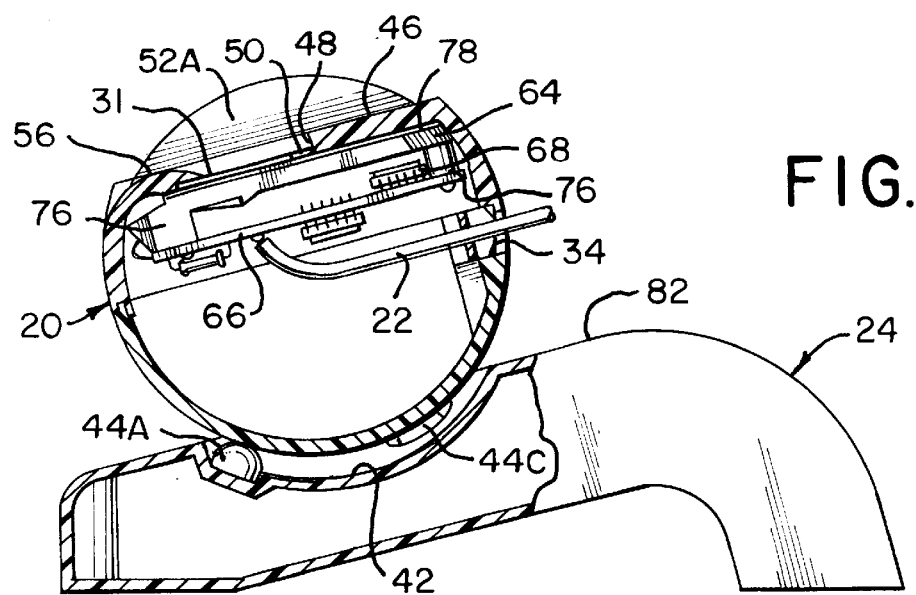
FIG. 4 is a side view of the ergonomic apparatus positioned within the base, partially broken away.

In FIG. 4, the ergonomic reader 20 is shown placed within the recess 42 of the base 24. The ergonomic reader 20 is illustrated as having been positioned with the planar surface 46 parallel to a top surface 82 of the base 24, although the invention is not so limited. As can be readily appreciated, the ergonomic reader 20 is universally positionable within the recess 42 upon protuberances 44A,B,C. As a result, the operator can position the platen 30 at an angle which is satisfactory for grasping the reader and inputting fingerprint data, as explained below in connection with certain exemplary applications.

FIG. 4 also depicts the physical relationship among the assembled components that constitute the uneven surface detection system 62 of FIG. 3. In particular, the printed circuit board 66 and optical plate 64 assembly are secured in position by the tape 78 immediately below the planar surface 46. In addition, the platen 30 is shown aligned with the aperture 48 so that a digit 32 placed on the top surface 31 of the platen 30 can provide input data to an image sensing device 68 mounted on the printed circuit board 66 along with a complement of other electronic components 70A,B, . . . N.

Figure 4A:
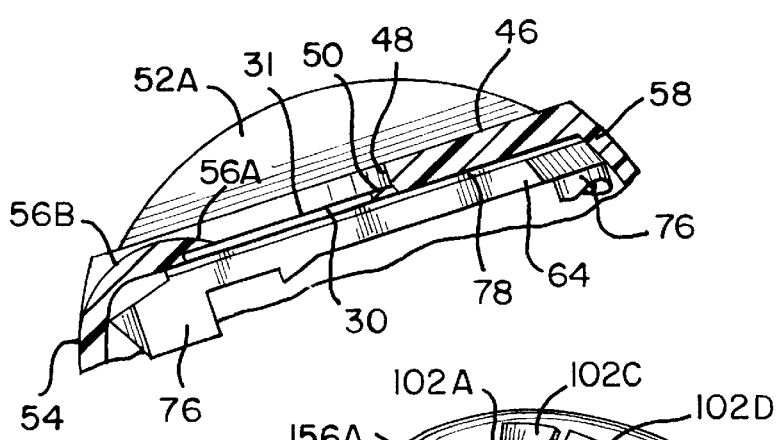
FIG. 4A is a partial expanded view of the ergonomic apparatus of FIG. 4 illustrating a contoured surface in detail.

Referring now to FIG. 4A, there is seen a partial expanded view of the contoured surface 56A,B provided in accordance with one aspect of the invention. The contoured surface 56 has a guide surface 56A adjacent the planar surface 46 disposed in abutting relationship to the platen 30. The guide surface 56A, in one respect, provides a guiding means for guiding the operator's digit 32 onto the top surface 31 of the platen 30. The guide surface 56A is adapted to provide its guiding function when formed in a manner sufficient to provide tactile feedback information to the operator that the digit 32 is not impinging on the edge 50 of the aperture 48. In the Figures, the guide surface 56A gradually slopes the planar surface 46 substantially to the plane of the top surface 31 of the platen 30. The contoured surface 56 also has a ramp surface 56B formed in the outside surface 54. The ramp surface 56B, in one respect, ramps the digit 32 onto the platen 30 at an angle such that the digit contacts or presses the top surface 31 of the platen 30 at an increased number of locations when the ergonomic reader 20 is grasped in the operator's hand 28. The ramp surface 56B is adapted to provide its ramping function when formed in a manner sufficient to allow the operator to place any digit 32 onto the platen 30 while grasping the ergonomic reader in his or her hand 28 in a natural or comfortable position, without the outside surface 54 of the ergonomic reader pressing against a region 57 of the hand 28 (see FIG. 8A). In the Figures, the ramp surface 56B is depicted as a curve of a sufficiently large radius to preclude the ergonomic reader from pressing against the region 57.

In FIGS. 5–8A, there are seen alternative embodiments of an ergonomic fingerprint reader apparatus according to the present invention. In these embodiments, features common to the first embodiment are given corresponding reference numerals. Otherwise than as specifically described below, these alternative embodiments share the inventive prehensile characteristics of the ergonomic reader 20 of FIGS. 1–4A.

Figure 5:
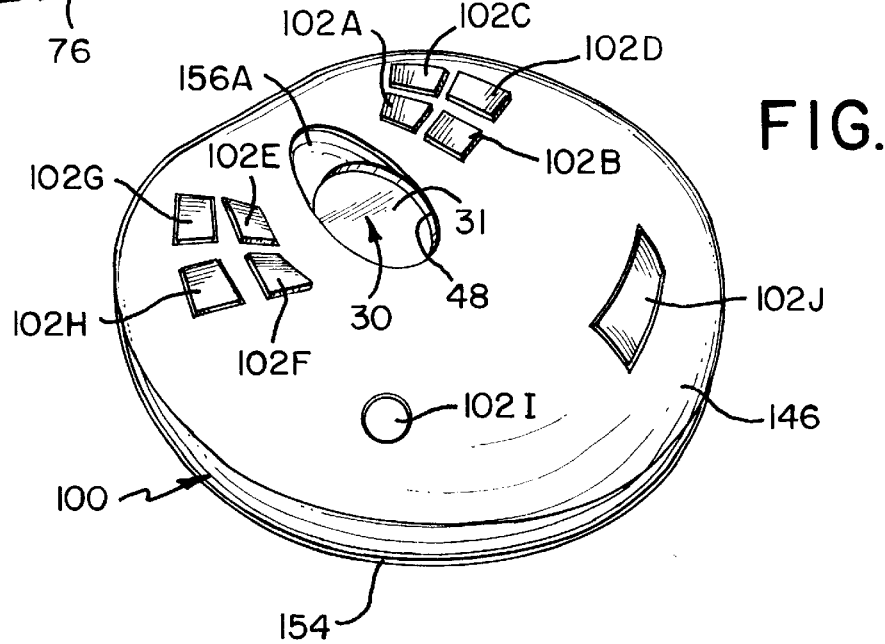
FIG. 5 is a top perspective view of a second embodiment of an ergonomic fingerprint reader apparatus according to the present invention used as a remote control unit.
Figure 6:
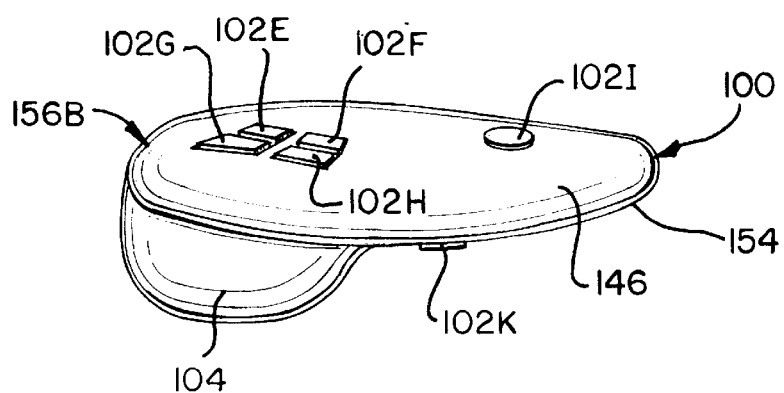
FIG. 6 is a side perspective view of the embodiment of FIG. 5.

In FIG. 5, the aperture 48 has been provided in a first surface 146 so that the operator has access to the platen 30 for inputting fingerprint data. In this embodiment, a second surface 154 is substantially opposite the first surface 146. Further, the reader 100 may comprise a wireless device for transmitting input data to a remote receiving unit. For example, the ergonomic reader 100 may be an infrared or radio frequency based remote control for operating integrated systems relating to security, stereo, and video applications, for controlling computers, televisions, or set-top boxes, or other devices. The ergonomic reader 100 may further include a plurality of buttons 102A,B, . . . N on the first surface 146 which may control, for example, power, volume up, volume down, channel up, channel down, identification select, menu up, menu down, menu select, or other features, depending on the particular application. As seen in FIG. 6, one or more buttons 102 may be located on the second surface 154 as well. Also seen in FIG. 6, the ergonomic reader 100 has a battery compartment 104, preferably accessible from the second surface 154 and located generally below the platen 30. The batteries in the compartment 104 add weight to a portion of the ergonomic reader 100 including the platen 30. As a result, substantially all of the weight of the ergonomic reader 100 is in the palm of the operator's hand 28 when grasped. Similar to the embodiment of FIGS. 1–4A, the first and second surfaces 146,154 of the ergonomic reader 100 may be grasped within the hand 28 while the digit 32 is or presses on the platen 30, thereby permitting the digit 32 to apply even pressure to the top surface 31 of the platen 30 so that a broad print of the digit 32 can be acquired.

Figure 7:
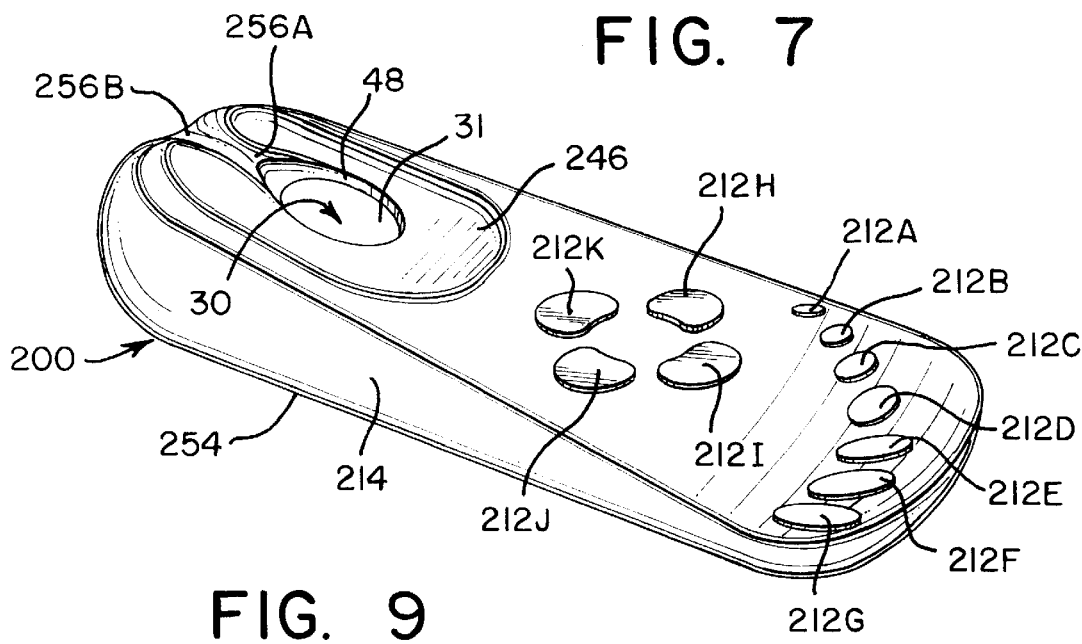
FIG. 7 is a perspective view of a third embodiment of an ergonomic fingerprint reader apparatus of the present invention used as a remote control unit.

In FIG. 7, an ergonomic reader 200 according to another embodiment is shown. The ergonomic reader 200 has a plurality of buttons 212 substantially the same as buttons 102. The ergonomic reader 200 may be used as a wireless controller, as previously described. Again, the ergonomic reader 200 of FIG. 7 includes an aperture 48 within the first surface 246 so that the platen 30 is exposed so that fingerprint data may be acquired from the operator's digit 32. Adjacent one margin of the ergonomic reader 200 is a contoured surface 256A,B which wraps from the first surface 246 to another surface (not shown) similar to the previously described contoured surface 56A,B. The ergonomic reader 200 has the characteristic prehensile shape of the foregoing embodiments so that the operator can grasp the controller along at least a second surface 254 and perhaps a third surface 214 as well.

Figure 8A:
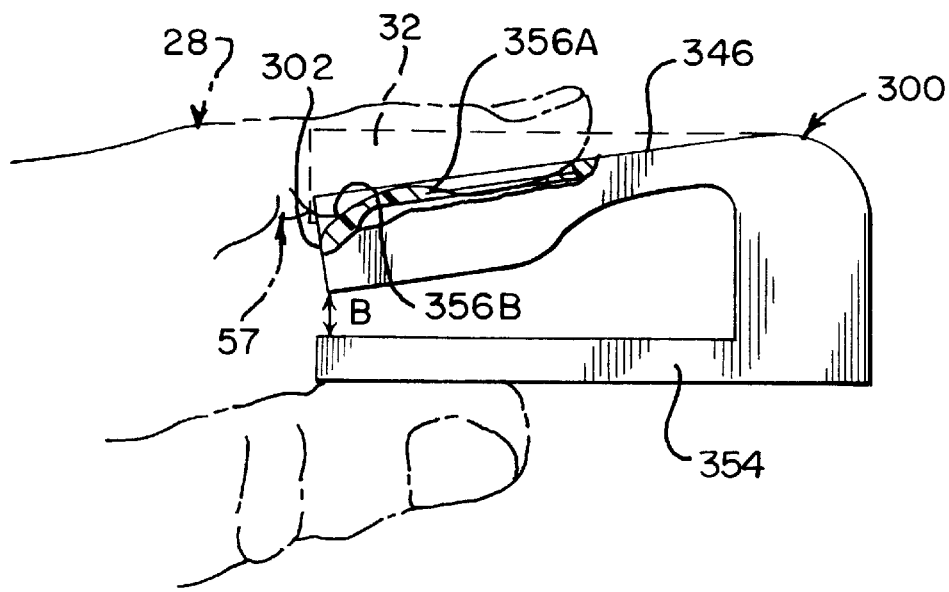
FIG. 8A shows the embodiment of FIG. 9 in use.
Figure 8:
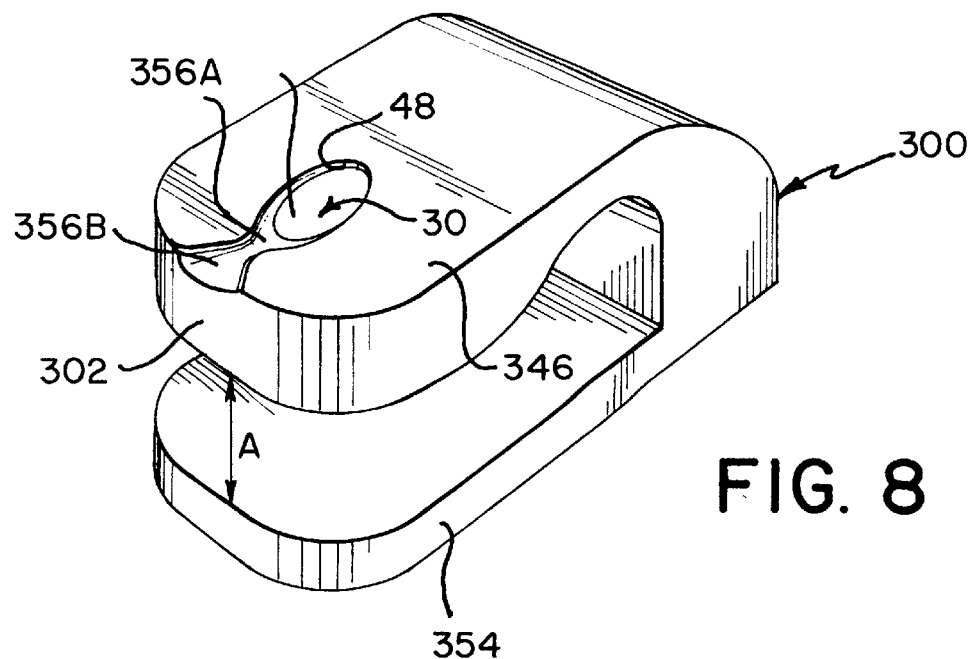
FIG. 8 shows a fourth embodiment of an ergonomic fingerprint reader apparatus according to the present invention.

FIG. 8 schematically illustrates an ergonomic reader 300 according to yet another embodiment of the invention. The ergonomic reader 300 may be used as a wireless controller, as previously described; however, to keep the illustration clear, neither the buttons nor the battery pack are shown. As in the previous embodiments, the ergonomic reader 300 has an aperture 48 within a first surface 346 so that the platen 30 is exposed. A contoured surface 356A,B wraps from the first surface 246 to another surface 302 for guiding and ramping the digit 32 to the top surface 31 of the platen 30, as previously described. The ergonomic reader 300 has the characteristic prehensile shape of the foregoing embodiments so that the operator can grasp the controller between the first and second surfaces 346,354 while the digit 32 is or presses on the platen 30. The ergonomic reader 300 is illustrated generally as a slotted controller, with a gap A defining the size of the slot. With reference now to FIG. 8A, it can be appreciated that the ergonomic reader 300 compresses in response to squeezing or grasping by the hand 28 so as to reduce the aperture of the slot to a smaller gap B. This mechanical motion may serve as a switch to trigger the image capture or acquisition process. Meanwhile, the digit 32—which has been previously positioned along the contoured surface 356 onto the platen 30—applies even pressure thereto so that a broad, even print of the digit 32 is acquired. The flex of the slot of the ergonomic reader 300 facilitates the acquisition of even fingerprint data. In particular, by squeezing the ergonomic reader 300, the operator provides a natural, uniform distribution of force to the device, and thereby transfers an even, broad fingerprint to the top surface 31 of the platen when the ergonomic reader 300 is squeezed.

The uneven surface detection system 62 may be activated to take a picture or capture an image of a digit 32 when the digit applies pressure to the platen 30, or when the digit covers a sufficient portion of the platen 30 to reduce the amount of light impinging on the image sensing device 68. In the former case, either the platen 30 or the housing of the ergonomic reader may act as a mechanical switch by hinging or flexing to trigger the image capture process. The platen 30 may hinge within the housing to trigger the image capture process, or may move with a portion of the housing, as shown in FIG. 8A in an equivalent hingelike manner.

The wireless remote controls of FIGS. 5–8A preferably transmit a compressed image of the acquired fingerprint data. These remote controls preferably use an infrared data link that operates significantly faster than traditional remote data transfer rates so that the remote need only be aimed at the receiving device for less than a second. The transmission rate should be chosen so that a compressed image of the fingerprint is transmitted to the receiving device in a time interval that is not noticeable to the operator of the remote. Of course, if the remote control transmits at a radio frequency, then the remote need not be aimed at the receiving device.

Processing of the fingerprint data and verification or authentication by matching to previously stored data should be performed at the set-top box or other receiving device so that the remote controls of FIGS. 5–8A conserve battery power. Further, this reduces unit production cost of the remote controls. Matching may be performed using a programmed processor, a comparator, logic gates, or similar device.

EXEMPLARY APPLICATIONS

1. Authentication System For Use With A Computer Terminal

In one exemplary application, the base 24 may be integral to or adjacent a computer terminal (not shown). As the operator manipulates the computer, the software may periodically request authorization or access privileges by requesting the operator to input fingerprint data at particular points in the program. In this manner, the program only provides information when the input fingerprint data matches within predetermined paramaters. The fingerprint match may be performed as to general characteristics or to minutiae, as understood by those skilled in the art. The match may be to prestored data within the base 24, the computer terminal, at a remote server or central station, or to prestored data on an identification card (e.g., driver's license, hospital identification card, government employee card, credit or smart card, etc.). If the matching of data is performed external to the base 24, then the acquired fingerprint data may be conveyed from the base 24 through the interface 40.

Regardless of whether the operator is standing or seated, and despite the particular left or right handed user preference, a uniform image of the digit 32 is reliably obtained in a repeatable fashion. Because the ergonomic reader 20 is universally positionable within the base 24, the operator can position the ergonomic reader 20 so that the platen is located in a position most comfortable to the operator for inputting fingerprint data, that is, with respect to the operator's relative position to the ergonomic reader, and with respect to the particular hand (and digit) that the operator has chosen to use for inputting fingerprint data. Once positioned, the operator merely wraps his or her hand 28 around the ergonomic reader 20 and may give a slight squeeze to provide uniform pressure to the platen 30. A broad, even image of the chosen digit 32 is thereby obtained. Moreover, because the protuberances 44A,B,C frictionally maintain the position of the ergonomic reader 20 within the base 24 until repositioned by the operator, once the operator has positioned the ergonomic reader 20 such that the platen 30 is located in a comfortable position, the operator can readily provide further fingerprint data in response to subsequent prompts by the software by grasping the ergonomic reader 20 without making any further adjustments. In this manner, the chosen digit 32 is repeatedly applied to the top surface 31 of the platen 30 in a comfortable position.

2. Authentication System For Use With A Point Of Purchase Terminal

In another exemplary application, the ergonomic reader 20 is used in combination with a point of purchase terminal for authenticating that the purchaser is authorized to use the credit, debit, smart card, or food stamps being presented at the point of sale.

Figure 9:
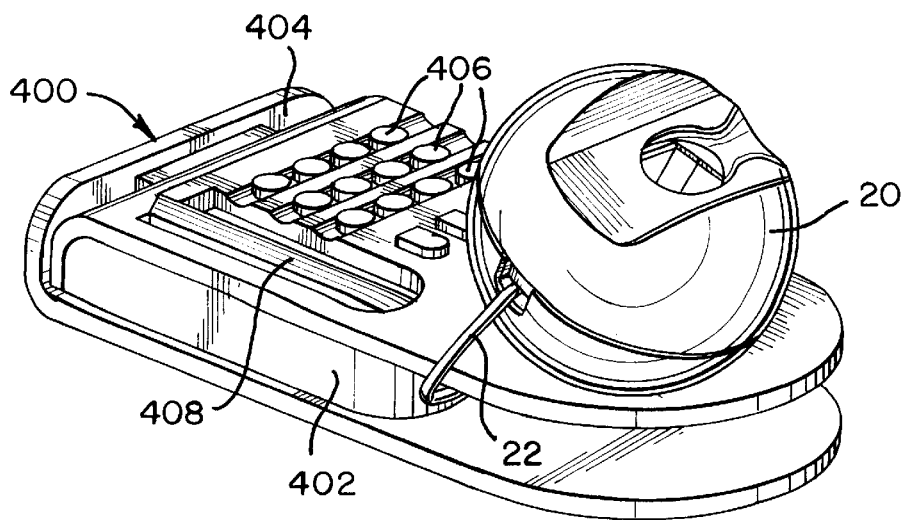
FIG. 9 is a perspective view of the tethered ergonomic apparatus of FIG. 1, shown connected to a modified base unit including a magnetic stripe card swipe device.

In FIG. 9, a point of purchase terminal 400 (POPT) is illustrated. The POPT 400 includes the ergonomic reader 20 connected to a base 402 by the tether 22. Of course, the tether 22 could be eliminated provided that a communication link is otherwise established between the ergonomic reader 20 and the base 402 or other authenticating device. In this regard, any of the wireless ergonomic readers 100, 200, and 300 would suffice. The base 402 has a recess therein similar to recess 42 to support the ergonomic reader 20 in the base 402 (not shown). The POPT 400 further has a card reader 404 so that the credit, debit, or smart card, may be swiped theretirough and data extracted therefrom. The card reader 404 can be replaced by other data extracting means, such as a scanning wand, for extracting information from the cards or from food stamps. Conventionally, the data extracted from such a card identifies a particular account so that the amount of the sale which is input using a plurality of calculator-like buttons 406 can be compared to the credit limit or debit balance for that account and the transaction either approved or denied, as displayed on a display screen 408. In accordance with an aspect of the invention, the card or stamps may include fingerprint image data stored thereon for comparison to image data sensed by the image sensing device 68 from the digit 32 placed on the platen 30. Alternatively, the comparison data may be stored remote to the card or stamps, as previously described. Regardless of where the comparison data is stored, the person presenting the card or stamps is compared with a store of authorized operators, for example, the card owner, his or her spouse, and perhaps their children to determine whether the actual person presenting the card is the authorized card holder. As a result, the discretion previously placed in the hands of the merchant, namely, to match signatures or perhaps a picture of the card owner, is removed. This will greatly reduce if not eliminate the exposure of creditors to fraud for these types of transactions. The POPT 400 has utility in retail stores, restaurants, resorts, vacation locals, etc. Further, when equipped with a cellular telephone link, the POPT 400 becomes a fully mobile authentication system for portable use when credit or debit card operators need to be authenticated, for example, with deliveries of food, merchandise, or other services, and at fairs, outdoor events, and temporary sales booths.

Typical credit cards that may be used with the POPT 400 include VISA, MasterCard, American Express, Mobile, Exxon, etc. Typical debit cards include those issued by commercial and savings banks. There are no smart cards known to be presently in use; however, such cards share the features of typical credit and debit cards, and provide one or more such accounts in a single card which may be used substantially as described above. Food stamps as used with the POPT 400 would include identifying information so that the food stamps can be associated with a particular person or family authorized to present the food stamps, and not necessarily the authorized person's fingerprint data.

3. Enrollment and Identification System For Receiving Benefits

The fingerprint data acquired using the previously described ergonomic readers can be used both to enroll an individual in a program, for example, welfare or medicaid, and to identify that the person seeking to claim the benefits is authorized to receive the benefits. During the enrollment of an individual, a supervisor or trusted employee is empowered to add or associate fingerprint data of the individual with other data for that individual, or some other person, in a central storage device, a local storage device, or on a card of the types previously described. The aforementioned other data may include name, address, age, fingerprint data, any prior enrollment and duration thereof, relation to the other person, etc. The individual enrolling in the system who is having his or her fingerprint data added or associated with his or her existing data, or with data of some other person, for example, his or her spouse, is acquired using one of the foregoing ergonomic readers and the acquired data is then stored onto the selected storage device. During identification, the individual's fingerprint data is again acquired, but this time is compared to the previously stored fingerprint data to determine whether the individual requesting benefits is entitled to receive the requested benefits. With this system, welfare, medicaid, and other types of fraud may be greatly reduced.

4. Broadcast, Cable, and Satellite Television Application

The previously described ergonomic readers, in particular, those of FIGS. 5–8A, can be used to identify fingerprint data or biometrics with particular operators to validate the operator and generate, for example, a personal identification number (PIN) that may then be passed to a processor in the set-top box for comparison and identification. The prompt for entering fingerprint data may be an on-screen text display or may be a transparent step as part of a menu selection process. The display or step is preferably programmed into the set-top box by way of software to appear whenever identification or authentication is required, for example, to obtain access or to restore operator preferences. As before, fingerprint data is entered by placing the digit 32 on the platen 30. The remote control determines when it has an adequate fingerprint image by locally performing processing, analysis, or both, and then transmits the image to the receiving device. The receiving device then notifies the operator that the fingerprint data has been received for validation by an on-screen icon, text, or by transmitting a signal to the remote control that indicates that the fingerprint data has been received. The comparison data is stored in reduced form in a storage device within the set-top box, unless perhaps such data is used for notarizing purposes, as described below. Confirmation of the validation may be by completing the channel selection, for example, allowing access to a restricted channel, or, in the case of programming that is to appear at a later time such as a pay-per-view movie that starts at the beginning of the next hour, by an icon or text on the screen.

The set-top box may restrict access to any of the following: up-front payment services including pay-per-view channels or special events; adult programming; parentally-controlled channels; home shopping services. However, the "authentication remote controls" of FIGS. 5–8A of the invention can be used to identify particular operators and allow them to access such restricted services. Further, the authentication remote control according to the invention may provide operator identification for restoring operator preferences including: pre-stored settings for audio (bass, treble, etc.), video (color, hue brightness), favorite channels, operator-tailored menus, viewing habits, etc. For example, the channels of particular interest to each individual, the so called "favorite channels" or channel priority configurations can be stored within a storage means in the set-top box (or side-car attached thereto) so that the individual can restore these configurations by informing the system that he or she is now in control of the authentication remote, as by inputting his or her fingerprint data on the platen 30.

To make use of the foregoing restrictions and tailorable preferences, it is preferred that at least one person be empowered as a "gate keeper." The gate keeper is initially set by entering fingerprint data for that person, perhaps in combination with a key. The key may be a numeric or alphanumeric code which is entered into the set-top box by the channel select buttons, or may be a card or conventional key. The gate keeper inters each of the other persons authorized to obtain access or set preferences. For example, as the gate keeper, a parent can inter a child into the system by setting the child's channel selection authority. In addition (or alternatively), the gate keeper can select a basic set of channels and preferences for children and guests who are not known to the system, that is, whose fingerprint data does not match any known data. The gate keeper can designate additional gate keepers that are equally empowered.

According to a further aspect of the invention, the fingerprint data can be used to notarize a transaction. The receiving device (or perhaps the remote control itself) may store credit, debit, or smart card account information for each identified operator for use in connection with purchases of merchandise, food, or cable related services (pay-per-view, special events, higher tier programming for a period of time, etc.). In response to suitable prompts, the operator makes a purchase though his or her set-top box. Credit card data, which may include the account number, type of card, expiration date, name of owner, etc., is conveyed along with compressed fingerprint data to serve as the operator's notarization that the transaction has been authorized against the identified credit, debit, or smart card account. The fingerprint data may be conveyed in the clear or scrambled, as understood by those skilled in the art of cryptography. The cable operator may serve as the credit authority and bill the operator directly for any purchases, or may forward the bill to the selected crediting institution, for example, VISA or American Express, provided that the fingerprint data included with the notarized transaction matches stored fingerprint data for that operator and the selected card, and is therefore authorized.

The term "fingerprint" as used in this specification refers to the ridge and groove patterns found on the digits of either hand, including the pinky, ring, middle, and index fingers as well as the thumb. The term "storage device" as used in this specification includes optical, electronic, magnetic, and bubble storage devices. By way of illustration only, such storage devices may include any of the following: CD ROM, RAM, SRAM, DRAM, PROM, EPROM, or floppy or hard disk drives. Also, the term "receiving device" as used hereinabove includes (1) set-top controllers, controller/descramblers, and side-cars attached thereto (more generally referred to above as "set-top boxes"), and (2) any other device not physically connected by wire or optical cable to the fingerprint reader which is equipped with an infrared or radio frequency receiver, for example, a computer, modem, multiplexer, etc. Finally, the terms "television set" includes any device which displays video programming, and "channel" refers to a particular program or source of programming.

While several embodiments have been shown and described, none is preferred as each has benefits for its intended function, as can be appreciated from the exemplary examples in which the individual may be operating devices from across a room by wireless link, may be seated at a computer terminal, etc.

From the foregoing description, it will be clear that the present invention may be embodied in other specific forms without departing from the spirit or essential characteristics thereof. Thus, for example, while certain embodiments of the ergonomic fingerprint reader apparatus have been shown and described, the invention is not limited to these embodiments. Other configurations are deemed to be within the scope of the invention provided they are adapted to be grasped while a finger presses on (or is placed on) the platen. Likewise, the exemplary applications are just that; and are not restrictive of the myriad applications for which the invention has utility. Thus, while a portion of the foregoing disclosure has been made with respect to certain exemplary applications, the invention is not so limited. The claimed invention stems from the entirety of this disclosure, and not from any specific portion thereof. The presently disclosed embodiments are therefore to be considered in all respects as illustrative and not restrictive, the scope of the invention being indicated by the appended claims, and not limited to the foregoing description.

What is claimed is:

1. A housing for a fingerprint acquisition device, comprising:

a platen having a platen surface adapted to be contacted by a digit of a person's hand, and first and second surfaces, the first surface having an aperture therethrough, the platen being disposed within the housing and the platen surface being in register with the aperture, the second surface being displaced from the first surface to provide a grasping surface, the housing being shaped to orient the digit relative to the platen to ensure a firm grip of the housing and also being shaped such that the second surface contacts four digits of the user's hand while a chosen, fifth digit is positioned on the platen in the first surface.

2. The housing of claim 1, further comprising a contoured surface adjacent the aperture.

3. The housing of claim 1, further including means for providing tactile feedback of the location of the digit on the platen to the person whose print is being acquired.

4. The housing of claim 3, wherein the tactile feedback means is disposed along the perimeter of the aperture.

5. The housing of claim 3, wherein the tactile feedback means includes an abrupt edge.

6. The housing of claim 5, wherein the abrupt edge terminates approximately 3 mm above the platen.

7. The housing of claim 1, wherein the second surface is substantially spherical.

8. The housing of claim 1, wherein the second surface is substantially opposite the first surface.

9. A housing for a fingerprint acquisition device, comprising:

a platen having a platen surface adapted to be contacted by a digit of a person's hand;

first and second surfaces, the first surface having an aperture therethrough, the platen being disposed within the housing and the platen surface being in register with the aperture, the second surface being displaced from the first surface to provide grasping surface, the housing being shaped to orient the digit relative to the platen to ensure a firm grip of the housing; and a base shaped to universally support the housing, the housing being universally positionable in the base to a preselected position for grasping the first and second surfaces and acquiring the print.

10. The housing of claim 9, wherein the base includes a processor for processing any acquired print of the digit.

11. The housing of claim 9, wherein the base further includes storage means for storing previously acquired prints, and matching means for matching any newly acquired print to any previously acquired prints.

12. A fingerprint acquisition device for acquiring a print from a person's digit, comprising:

a housing having first and second exterior surfaces, the housing enclosing:

a platen having a platen surface;

a light source for irradiating the platen surface and any digit thereon with light;

means for conducting light from the irradiated platen surface; and image sensing means for sensing the conducted light, the first exterior surface having an aperture therethrough, the platen surface being disposed in register with the aperture, the second exterior surface being displaced from the first exterior surface to provide a grasping surface, the housing being shaped to orient a digit relative to the platen to ensure a firm grip of the housing and being shaped such that the second surface contacts four digits of the user's hand when a chosen, fifth digit is positioned on the platen in the first surface.

13. The fingerprint acquisition device of claim 12, wherein any print acquired at the image sensing means is conveyed to a remote location by one of a conductive wire, optical cable, infrared, inductive pickup, and radio frequency.

14. The fingerprint acquisition device of claim 12, further comprising compression means for compressing any print acquired at the image sensing means.

15. The fingerprint acquisition device of claim 12, further comprising data extracting means for extracting data from a credit card or food stamp.

16. The fingerprint acquisition device of claim 15, further comprising matching means for matching any acquired print to the extracted data from the credit card or food stamp.

17. The fingerprint acquisition device of claim 16, further comprising verification means for indicating that the acquired print and the extracted data match.

18. The fingerprint acquisition device of claim 15, wherein any print acquired at the image sensing means and any extracted data from the credit card or food stamp are conveyed to a remote location by one of a conductive wire, optical cable, infrared, inductive pickup, and radio frequency for matching.

19. The fingerprint acquisition device of claim 18, further comprising indicating means for indicating that the remote location has matched the acquired print and the extracted data.

20. The fingerprint acquisition device of claim 15, wherein the data extracting means is one of a card reader and scanning wand.

* * * * *

UNITED STATES PATENT AND TRADEMARK OFFICE
CERTIFICATE OF CORRECTION

PATENT NO.   : 6,041,134
DATED        : March 21, 2000
INVENTOR(S)  : John Michael Merjanian It is certified that error appears in the above-identified patent and that said Letters Patent is hereby corrected as shown below:

Title page,
Item [63], after "Related U.S. Application Data" change the text to read
-- Continuation of application No. 08/836,242, filed as application No. PCT/US95/ 14374, Oct. 28, 1995, Pat. No. 5,920,642, which is a continuation of application No. 08/331,212, filed Oct. 28, 1994, Pat. No. 5,546,471. --;

Column 1,
Lines 4-7, revise to read -- This is a continuation of application No. 08/836,242, filed Apr. 28, 1997, now U.S. Pat. No. 5,920,642, which is a U.S. national phase application based on PCT/US95/14374, filed Oct. 28, 1995, which is a continuation of U.S. application No. 08/331,212, filed Oct. 28, 1994, now U.S. Pat. No. 5,546,471. --

Signed and Sealed this

Third Day of September, 2002

*Attest:*

*Attesting Officer*

JAMES E. ROGAN
*Director of the United States Patent and Trademark Office*